United States Patent [19]

Messina

[11] Patent Number: 5,783,204
[45] Date of Patent: *Jul. 21, 1998

[54] DEER REPELLENT AND METHOD

[76] Inventor: James Messina, 58 Califon Rd., Long Valley, N.J. 07853

[*] Notice: The term of this patent shall not extend beyond the expiration date of Pat. No. 4,965,070.

[21] Appl. No.: 748,757

[22] Filed: Nov. 14, 1996

[51] Int. Cl.$^6$ ................................................ A01N 25/32
[52] U.S. Cl. .................. 424/406; 424/405; 424/407; 424/418; 424/421; 514/920
[58] Field of Search ............................. 424/405, 406, 424/407, 418, 421; 514/920, 479

[56] References Cited

U.S. PATENT DOCUMENTS 4,965,070  10/1990  Messina ........................ 464/581
5,183,661  2/1993   Messina ........................ 464/405
5,368,866  11/1994  Loulas .......................... 464/581

OTHER PUBLICATIONS

Besser et al. Pesticides & Controls. Trans. N. AM. Wildlife Conf. 24, 166–73 (1959) from Biol. Abstr. 36 #29607 (1961).

Primary Examiner—Neil S. Levy
Attorney, Agent, or Firm—Graham, Curtin & Sheridan; Richard T. Laughlin, Esq.

[57] ABSTRACT

A deer repellent formulation and method for warding off a deer from a shrub or plant. The formulation is an admixture of water, eggs, thiram and an adhesive. The formulation can be applied to a support medium such as clay or a length of rope and then associated with the vegetation to be protected.

6 Claims, No Drawings

DEER REPELLENT AND METHOD

The invention generally relates to a deer repellent and, in particular, the invention relates to a deer repellent composition which can be applied to a wide range of surfaces and to a method for use of such a composition.

BACKGROUND OF THE INVENTION

The prior art deer repellent formulation is described in U.S. Pat. No. 4,965,070, issued October 23, 1990 to the same inventor as this application. The prior art formulation consisted essentially of by volume: 68 to 90% water; 6 to 10% thiram; 0.5 to 2% chicken eggs; 1 to 2% liquid hot sauce; 2 to 16% adhesive to aid in adhering to vegetation; and 0.5 to 2% coloring dye. U.S. Pat. No. 4,169,902 of DeLuca teaches a water spray medium and thiram for a repellent.

One problem of the prior art deer repellent formulation is that, although the ingredients are common materials, it requires approval of the Environmental Protection Agency which involves long and costly tests. Since formulations of this type are applied by small companies, such as landscape gardeners, the obtaining of approval from the EPA is financially prohibitive. Further, the prior art materials have a limited effective life, and the odor of the formulation can limit its acceptance.

OBJECTS OF THE INVENTION

One object of the present invention is to provide an improved deer repellent formulation for application to a shrub, plant or the like which can be acceptable under the Environmental Protection laws.

Another object of the invention is to provide a deer repellent formulation more acceptable to humans.

Other objects and the advantages of the invention will appear from the following description.

SUMMARY OF THE INVENTION

According to the present invention, a deer repellent formulation and method for its use are provided. The formulation consisted essentially of 68 to 90% water; 6 to 10% thiram; 0.5 to 2% chicken eggs; 2 to 16% adhesive to aid in adhering to vegetation; and 0.5 to 2% coloring dye. All of the percentages are by volume of the composition. This formulation has proven effective and is approved by the Environmental Protection Agency.

DESCRIPTION OF THE PREFERRED EMBODIMENT

The preferred deer repellent formulation is 85% water; 8% thiram; 1% chicken eggs; 1% coloring dye; and 5% adhesive to aid in adhering to vegetation or the carrier material.

Thiram is the coined common name for the chemical tetraethylthiram with the formula $C_6H_{12}N_{23}$, and is commonly used as a fungicide and as a seed disinfectant. Thiram is packaged in 75% concentration dry.

The thiram is mixed with water to produce a water solution. A selective weight of chicken eggs which are deshelled, or removed from their shells, is added to the solution. The eggs act as a deterrent agent. A coloring dye is an optional addition to the solution for blending the deer repellent assembly with the landscape. A coloring dye, such as that sold in under the name "Greenzit," can be used. The adhesive, such as that sold under the trademark "NU-FILM-P" or the like can be used. In particular, the adhesive is used for a deer repellent assembly, which is exposed to rain or snow.

The composition of the invention can be utilized in the manner described in my U.S. Pat. No. 5,183,661 issued on Feb. 2, 1993 to James Messina. The formulation of the invention can be applied to a support medium such as a solid braid, number 8, cotton and polyester, ¼ inch diameter, sash cord rope of 100 foot length, which is sold by the Lehigh Group, Allentown, Pa. 18105, United States. The support medium can also be a clay material, which ranges in size of clay granules or particles, from dustless fine granules to about ¼ inch overall diameter or thickness granules. The clay material comes packaged in a 0.20 pound bag, which is made of a finely woven cloth material and which has a drawstring along an open top edge thereof, and which has a size of about 4 inches in height by about 3 inches in width when flat. The drawstring threads through spaced holes located about ½ inch down from the bag top edge.

The deer repellent assembly of support rope and formulation can be wrapped around a shrub or plant or strung between shrubs and plants. The deer repellent assembly of support medium clay material and formulation can be distributed under and around shrubs and plants, or the like.

It is noted that 16 fluid ounces of deer repellent formulation are sufficient to wet the 100 foot length of ¼ inch diameter rope. Also, 11 fluid ounces of deer repellent formulation are sufficient to wet throughout the one pound of clay granules. A shorter rope length requires proportionally less fluid ounces of formulation based upon rope length and rope cross-section areas. Less than one pound of clay granules medium requires proportionally less fluid ounces of formulation based upon medium volume.

EXAMPLE I

The deer repellent formulation in the preferred embodiment for outdoor application as follows:

128 fluid ounces of water, 12 fluid ounces of thiram, 2 chicken eggs, green coloring dye in an amount to produce the desired color, and adhesive in a quantity sufficient to adhere to the plant.

EXAMPLE II

The deer repellent formulation in the preferred embodiment for outdoor application as follows:

128 fluid ounces of water, 12 fluid ounces of thiram, 2 chicken eggs,

1% green coloring dye in an amount to produce the desired color, and

5% adhesive to adhere the composition to the plant.

EXAMPLE III

The deer repellent assembly in the first embodiment is shown below:

a 100 foot length of support rope of ¼ inch diameter, and of cotton and polyester, solid braid material;

16 fluid ounces of deer repellent formulation, consisting of about 15 fluid ounces of water and about 0.125 ounces by weight of deshelled chicken eggs and about 0.968 ounces by weight of 75% thiram dry and an adhesive in a quantity sufficient for adherence to the support rope and a coloring dye in an amount sufficient to produce a desired color.

The said deer repellent formulation is distributed evenly along the support rope length.

EXAMPLE IV

The deer repellent assembly in the second embodiment is shown below:

one pound by weight of clay granules in a particle size distribution from dustless fine particles to about ¼ inch overall thickness particles for a support medium;

11 fluid ounces of deer repellent formulation consisting of about 10 fluid ounces of water and about 0.086 ounces by weight of deshelled chicken eggs and about 0.665 ounces by weight of 75% thiram dry and an adhesive in a quantity sufficient for adherence to the support medium clay granules and a coloring dye in an amount sufficient to produce a desired color.

The deer repellent formulation is mixed with the support medium clay granules.

While the invention has been described in its preferred embodiment, it is to be understood that the words which have been used are words of description rather than limitation and that changes may be made within the purview of the appended claims without departing from the true scope and spirit of the invention in its broader aspects.

What is claimed is:

1. A deer repellent formulation consisting essentially of 68 to 90% water, 6 to 10% of thiram; 0.5 to 2% eggs; 0.5 to 2% coloring dye; and 2 to 16% adhesive.

2. A deer repellent formulation consisting essentially of 85% water, 8% of thiram; 1% chicken eggs; 1% coloring dye; 5% adhesive.

3. The deer repellent formulation as defined in claim 1 wherein 16 fluid ounces of the formulation is carried by a 100 foot length of support rope of ¼ inch diameter and of cotton and polyester solid braid material and the formulation consists of about 15 fluid ounces of water, about 0.125 ounces by weight of deshelled chicken eggs and about 0.968 ounces by weight of 75% thiram dry and an adhesive in a quantity sufficient for adherence to the support rope;

said deer repellent formulation being about evenly distributed along the length of the support rope.

4. The deer repellent composition as defined in claim 1 supported on one pound by weight of clay granules in a particle size distribution from about dustless fine particles to about one-quarter inch overall thickness particles;

said formulation being about evenly distributed throughout the support medium clay granules.

5. A method of repelling deer from a shrub or plant including the steps of:

preparing a deer repellent formulation by admixing about 15 fluid ounces of water, about 0.125 ounces by weight of deshelled chicken eggs and about 0.968 ounces by weight of 75% thiram dry and an adhesive;

forming a support medium for the formulation;

distributing the formulation evenly on the support medium; and disposing the support medium on and about the shrub or plant.

6. The method of claim 5, wherein the formulation measures about 16 fluid ounces per 100 foot of rope length containing per 16 fluid ounces:

eggs at about 0.125 ounces by weight;

thiram at about 0.968 ounces by weight; and water at about 15 fluid ounces prior to evaporation thereof.

* * * * *